United States Patent [19]

Koning et al.

[11] Patent Number: 4,534,825
[45] Date of Patent: Aug. 13, 1985

[54] METHOD OF MAKING AN ELECTROCHEMICAL SENSING CELL

[75] Inventors: Gerrit Koning, Vries; Piet Bergveld, Enschede, both of Netherlands

[73] Assignee: Cordis Europa, N.V., Roden, Netherlands

[21] Appl. No.: 587,819

[22] Filed: Mar. 9, 1984

Related U.S. Application Data

[62] Division of Ser. No. 242,351, Mar. 10, 1981, Pat. No. 4,478,222.

[30] Foreign Application Priority Data

Mar. 10, 1980 [NL]  Netherlands ............. 8001420

[51] Int. Cl.$^3$ ............................................. G01N 27/46
[52] U.S. Cl. ...................................... 156/644; 156/654; 156/659.1; 29/570; 204/403; 204/416; 128/635; 357/25
[58] Field of Search ............... 156/644, 652, 650, 625, 156/659.1, 654, 656, 657; 29/570, 580, 590, 591, 578; 204/400, 403, 1 T, 418, 429, 416; 357/25; 128/635

[56] References Cited

U.S. PATENT DOCUMENTS 3,476,670 11/1969 Weiner ................. 204/195
3,924,321 12/1975 Cook, Jr. et al. ............. 29/580
4,020,830 5/1977 Johnson et al. ............. 204/418 X
4,041,933 8/1977 Reichenberger ............. 128/2 E
4,152,233 5/1979 Chand .................. 204/1 T X
4,221,567 9/1980 Clark et al. .............. 23/230 B

FOREIGN PATENT DOCUMENTS 0015075 9/1980 European Pat. Off.
0036171 9/1981 European Pat. Off. ...... 128/635

Primary Examiner—Edward Kimlin
Assistant Examiner—Ramon R. Hoch
Attorney, Agent, or Firm—Henry W. Collins

[57] ABSTRACT

An in vivo electrochemical monitoring device is formed by a catheter-like member which terminates in a closed end having a wall with a fixed opening to admit fluid to be tested, such as blood in an artery. An electrochemical sensor, such as an ISFET device for monitoring the concentration of a particular ion in blood, is mounted inside the tube at a fixed location below the opening preferably a larger sensing chamber. An infusion channel in the tube is arranged to flood the sensor with a fluid of known chemical properties so that the sensor output can be calibrated. Under pressure the calibration fluid expels the test fluid out of the tube or chamber via the fixed opening. A method of constructing a suitable chamber on an ISFET wafer is also disclosed.

5 Claims, 7 Drawing Figures

METHOD OF MAKING AN ELECTROCHEMICAL SENSING CELL

This is a division, of application Ser. No. 242,351, filed Mar. 10, 1981, now U.S. Pat. No. 4,478,222, issued Oct. 23, 1984.

BACKGROUND OF THE INVENTION

The invention relates generally to electrical sensor assemblies used in in vivo measurement of chemical parameters in a test fluid, such as blood in an artery, and in particular to calibration systems for chemically sensitive electrodes used in catheters, for example.

Electrochemical sensing devices, such as ion sensitive field effect transistors (ISFETS) are finding numerous applications in measuring the chemical properties of fluids. One such application has been the use of an ISFET device in conjunction with an ion selective membrane for performing continuous in vivo measurement of the concentration of a particular ion in the blood. The sensor is mounted on a catheter which is fed into an artery via a conventional catheter introducer. While extremely sensitive to variations in ion concentration, the ISFET device, like other electrochemical sensors, suffers from drift which seriously undermines the accuracy of the readings. Frequent recalibration of the output device connected to the sensor essentially removes these inaccuracies. One method of calibration which has been used in the past is to draw a sample of blood, for example, from a separate arterial puncture or by means of a syringe connected to a side arm assembly of the catheter containing the sensor and actually measuring the electrochemical activity of the ion of interest using standard laboratory techniques. Alternatively, the sensor itself may be removed for in vitro calibration in a fluid of known exact ion concentration. The ideal system, however, would perform recalibration in vivo without laboratory analysis.

One system which has been proposed for performing in vivo calibration of an electrochemical sensor is referred to in U.S. Pat. No. 4,016,866 to Lawton, involving a retractable sensing electrode carried by an insertion catheter. To perform measurements, the electrode is extended axially out of the insertion catheter. For recalibration, the sensing electrode is retracted into the insertion catheter to an infusion chamber where it is contacted with calibrating solution furnished by a drip line in which a reference electrode also contacts the calibrating solution. Following calibration the sensor is protracted to the exterior measurement position. The electrode must be accurately aligned with an opening in the end of the insertion catheter and the opening must be large enough to allow the electrode to freely pass through the opening in either direction. Thus the opening must be larger than the electrode. Moreover, the need for axial retractability requires a rather complicated mechanism involving sealing glands and guard tubes to maintain a sliding seal. The mechanical action of the sensor places certain constraints on the mounting arrangement of the sensor and generally increases the risk of mechanical damage to the sensor and electrical connections to the sensor. Because of the size of the opening in the insertion catheter, there is also a possibility of blood flowing into the catheter and mixing with the calibration liquid unless the calibration liquid.

SUMMARY OF THE INVENTION

The general object of the invention is to provide a structural arrangement for an electrochemical sensor such as an ISFET device in a catheter-like tube in which the sensor remains at a fixed location in a chamber which functions both as a calibration chamber and as a test fluid chamber. In accordance with the invention, an in vivo electrochemical monitoring device is formed by a catheter-like member which terminates in a closed end having a wall with a fixed opening to admit fluid to be tested, such as blood in an artery. An electrochemical sensor, such as an ISFET device for monitoring the concentration of a particular ion in blood, is mounted inside the tube in a fixed location below the opening, preferably in a larger sensing chamber. An infusion channel in the tube is arranged to flood the sensor at its fixed location with a fluid of known chemical properties for calibration. Under pressure, the calibration fluid expels the test fluid out of the tube or chamber via the fixed opening. Maintaining a positive flow of calibration fluid at a controlled pressure keeps the test fluid out of contact with the sensor while bathing the sensor in the known ion concentration.

According to a further aspect of the invention, a method of constructing a suitable chamber on an ISFET wafer includes applying a first layer of soluble material, covering the first layer with a second layer of another material, making a hole through the second layer and removing the first layer entirely by introducing solvent through the hole in the second layer.

DESCRIPTION OF THE PREFERRED EMBODIMENTS

Figure 1:
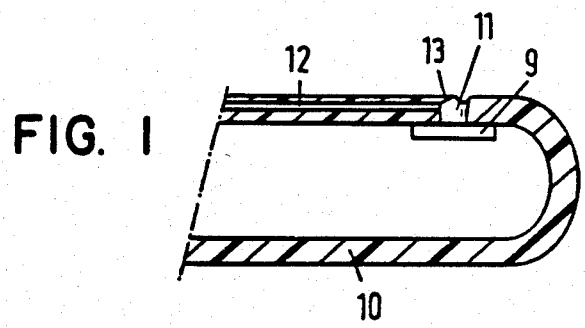
FIG. 1 is a diagramatic longitudinal sectional view of a closed tubular catheter having a chemically sensitive sensor bonded to the sidewall.

In the following examples the electrochemical sensor comprises an ISFET with a source and drain electrode and an Ag/AgCl reference electrode. In FIG. 1, a closed tubular catheter 10 made of flexible synthetic plastic material has a small opening 11 formed in the sidewall thereof which is sealed off on the inside of the catheter 10 by an ISFET device 9 which is bonded to the inner wall of the catheter by means of a suitable adhesive, for example. The catheter 10, over a limited circumferential extent, is double-walled to form an infusion channel 12 which leads to the opening 11. The end portion 13 of the outer wall of the channel 12 extends part way over the opening 11 so as to constrict the opening 11 at the outer surface of the catheter 10. The compartment or chamber formed by the opening 11, end portion 13 of the wall and the ISFET 9 functions as a calibration compartment for the ISFET. When calibration liquid of a known chemical composition is forced through channel 12, the liquid, for example blood, present in the opening or chamber 11 will be expelled. Thus opening 11 will become entirely filled with calibration liquid. While the supply of calibration liquid is being maintained under controlled pressure, the ISFET electrical output can be calibrated. When the flow of calibration liquid is stopped or reversed, the opening 11 functioning as a small compartment refills with blood and measurement can be continued. The calibration step can be automatically cycled if desired.

Figure 2:
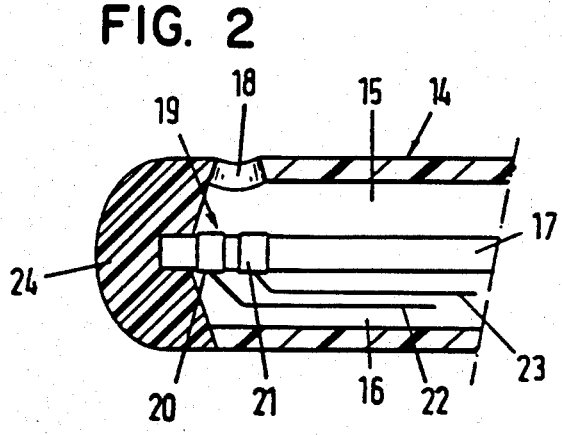
FIG. 2 is a diagramatic longitudinal sectional view of a bilumen tubular catheter in which the sensor is mounted on a common partition.
Figure 3:
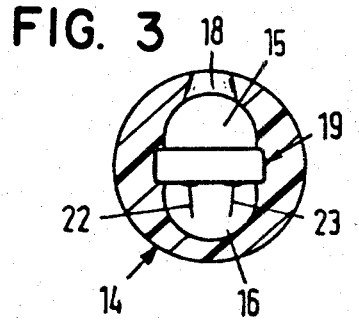
FIG. 3 is a cross-sectional view taken generally at the location of the sensor of FIG. 2.

In the embodiment of FIG. 2, the catheter 14 has two lumina 15 and 16 separated by a common partition 17. Adjacent to the end of catheter 14, a tapered opening 18 is formed in the catheter wall. Under the opening 18, the sensor 19 with ISFET 20 and Ag/AgCl reference electrode 21 with respective electrical leads 22 and 23, are mounted in partition 17. During measurement, channel 15, formed by the lumina in communication with opening 18, contains blood which is in contact with the sensor 19. By supplying calibration liquid through channel 15, the blood present therein is expelled and the sensor can be calibrated. When the supply of calibration liquid is discontinued, blood will again flow into channel 15 and the unit will return to the measuring phase. The catheter end 24 may take the form of a loose cap which, after sensor 19 has been installed, can be placed in position on the partition and secured, for example, with adhesive.

Figure 4:
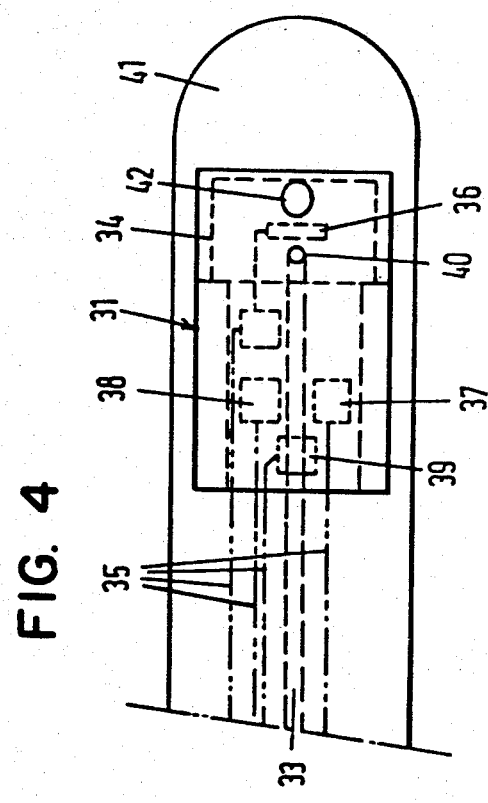
FIG. 4 is a plan view of the end of a tubular catheter according to the invention having a separate infusion tube.
Figure 5:
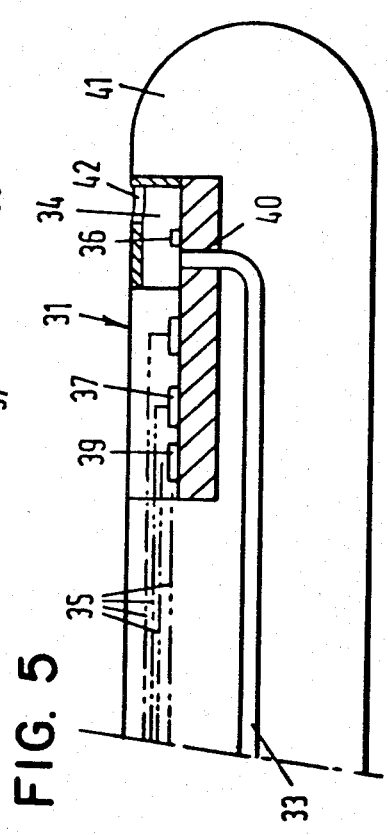
FIG. 5 is a diagramatic longitudinal sectional view of the catheter of FIG. 4.

In FIGS. 4 and 5, an ISFET 31 is mounted in an opening in the wall of the catheter 41. ISFET 31 comprises source electrode 37, drain electrode 38 and bulk contact 39, with leads 35. The ion-sensitive portion of the ISFET is housed in a chamber 34 formed by the ISFET and adjacent catheter wall, which also accommodates the Ag/AgCl reference electrode 36. An aperture 40 is formed through the bulk of the ISFET terminating in chamber 34, to which infusion tube 33 is connected for supplying calibration liquid to the chamber. At the top the chamber 34 has an aperture 42 for incoming blood or outgoing calibration liquid.

Figure 6:
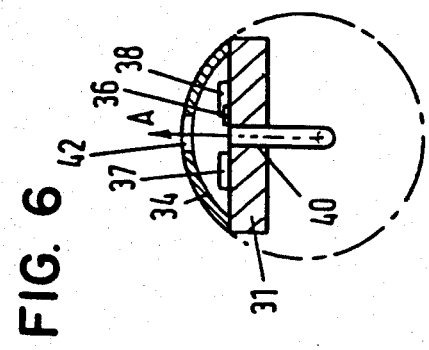
FIG. 6 is a diagramatic cross-sectional view of the tubular catheter and sensor of FIG. 4.

During the measuring phase, chamber 34 is entirely filled with blood. In order to switch over to calibration of the ion-sensitive electrode, a stream of calibration liquid is supplied to chamber 34 in excess of blood pressure. If desired, the pressure driving the calibration liquid may be adjusted automatically as a function of blood pressure. The blood present in chamber 34 is expelled through aperture 42. So long as adequate pressure is maintained, calibration liquid will flow in direction A, as indicated in FIG. 6, out of the opening 42. When, after the calibration, a reduced pressure, or at any rate no excess pressure, is established in chamber 34, the chamber will again be entirely filled with blood, and measurement can be resumed. Calibration and measurement can be performed automatically in pre-programmed repetition.

Tube 33 is not an essential component. The calibration liquid can be supplied through catheter tube 41 provided that the leads 35 are suitably insulated.

Figure 7:
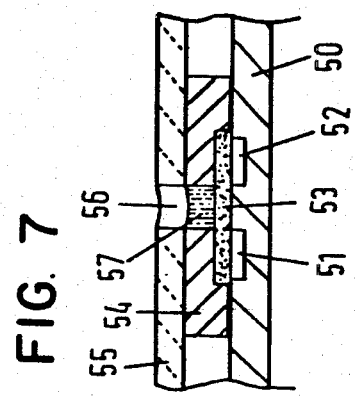
FIG. 7 is a diagramatic sectional view illustrating the construction of a calibration compartment on an ISFET wafer.

The chamber for the calibration compartment can be formed directly on an ISFET wafer using the same integrated circuit technology that is used for making the ISFET itself. A few additional steps are required for making the chamber. As shown in FIG. 7, the ionsensitive portion (the gate) with the source electrode 51 and the drain electrode 52 of the ISFET 50 are covered with a temporary protective layer 53 of a material that can easily be dissolved or etched. Subsequently a layer 54, preferably of a conductive material, e.g., a metal or polysilicon, is applied on top of and around layer 53. Next a mask 55 having an opening 56 therein is laid on top of conductive layer 54, and through opening 56 an etching agent is supplied for etching an opening 57 in layer 54. Finally, a solvent for layer 53 is supplied through opening 57, and layer 53 is dissolved and removed, leaving an empty chamber.

Although an insulating material may be selected for layer 54, the use of a conductor is preferred because the chamber formed therein functions as a Faraday cage.

It is of advantage, after forming the chamber, to cover the unit of FIG. 7 with a layer which promotes its biological compatability without unduly affecting its response period. A preferred material for this purpose is a hydrogel material.

The chamber 34 of FIGS. 4–6 may be formed in the manner of FIG. 7 or by fixing a separately manufactured apertured chamber wall to the ISFET with adhesive, for example.

The utility and applicability of the invention is not limited to ISFET devices. The possibility of neutralizing the effect of the drift phenomena by continual recalibration in a standard medium in a calibration/test chamber might also be beneficial with other types of electrochemical sensors.

Among the many advantages of the invention is the use of a single location and single chamber for both measuring and calibrating the sensor whereby, without mechanical intervention, the contents of the chamber are solely determined by the pressure applied to the infusion channel, thus facilitating an automatic calibration cycle. The simple construction of the sensing apparatus according to the invention results in an inexpensively constructed reliable instrument. In addition, the Faraday cage effect of forming the calibration chamber in conductive material reduces the sensitivity of the instrument to external and internal (bio) sources of electrical interference. The constant access to infusion fluids enhances the biological compatability of the sensor by regularly washing it, for example, with heparinated liquid. In addition, the construction enables automatic testing of electrical sensitivity via a pulse on the reference electrode which is in a fixed electrolytic trough arrangement.

The foregoing description and drawings are intended to be illustrative not restrictive, the scope of the invention being indicated by the appended claims.

We claim:

1. A method of making a sensing cell for a chemically sensitive probe for measuring the properties of biological fluids in vivo, comprising the steps of producing a wafer comprising an ISFET with spaced source and drain regions spanned by an ion-sensitive gate portion, covering said source and drain regions and gate portion of said ISFET with a temporary first layer of soluble material, covering said temporary first layer with a second layer of relatively insoluble material, defining an opening in said second layer directly above said gate region, and removing said temporary first layer which covers the source and drain regions and the gate portion by introducing a solvent through said opening to dissolve said first layer, thus forming a sensing chamber encompassing the source and drain regions as well as the gate portion of said ISFET.

2. The method of claim 1, wherein said second layer is electrically conductive.

3. The method of claim 1, further comprising the step of forming an infusion through-hole through the wafer leading into said sensing chamber, whereby a known fluid can be introduced through said through-hole into said chamber for calibration in vivo.

4. The method of claim 1, wherein said opening formed in said second layer is narrower than said chamber formed by removing said first layer.

5. The method of claim 1, further comprising the step of covering said cell with a layer of hydrogel to promote biological compatability.

* * * * *